United States Patent [19]
Kawazu et al.

[11] Patent Number: 6,015,925
[45] Date of Patent: Jan. 18, 2000

[54] ANTIFUNGAL AGENTS

[75] Inventors: Yukio Kawazu; Toshimitsu Suzuki; Masayuki Yuasa; Yuichi Yokomizo; Toshiro Majima; Takao Ito; Takuji Nakashima; Akira Nozawa, all of Yokohama, Japan

[73] Assignee: Pola Chemical Industries, Inc., Shizuoka, Japan

[21] Appl. No.: 09/158,093

[22] Filed: Sep. 22, 1998

[51] Int. Cl.[7] .................................................. C07C 211/00
[52] U.S. Cl. ........................................... 564/316; 564/321
[58] Field of Search ..................................... 564/316, 321

[56] References Cited

FOREIGN PATENT DOCUMENTS

| | | |
|---|---|---|
| 9-169710 | 6/1997 | Japan . |
| 9-169711 | 6/1997 | Japan . |
| 9-255633 | 9/1997 | Japan . |
| 9-255634 | 9/1997 | Japan . |
| 9-255643 | 9/1997 | Japan . |
| PCT/JP98/03487 | 8/1998 | WIPO . |
| PCT/JP98/03563 | 8/1998 | WIPO . |

Primary Examiner—Paul J. Killos
Attorney, Agent, or Firm—Oblon, Spivak, McClelland, Maier & Neustadt, P.C.

[57] ABSTRACT

This invention relates to compounds represented by the following formula (1):

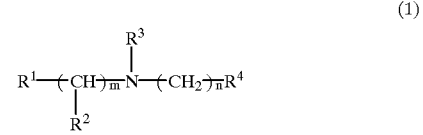

(1)

wherein $R^1$ represents a substituted or unsubstituted aromatic hydrocarbon group having 6 to 18 carbon atoms, $R^2$ represents a hydrogen atom or a substituted or unsubstituted aromatic hydrocarbon group having 6 to 18 carbon atoms, $R^3$ represents an alkyl group having 1 to 4 carbon atoms, $R^4$ represents a substituted or unsubstituted phenyl group or an aliphatic hydrocarbon group containing at least four π electrons, and m and n individually represent integers of from 1 to 4, or salts thereof, and also to compositions containing the same. These compounds have antifungal activities and are useful as drugs and the like.

6 Claims, No Drawings

ANTIFUNGAL AGENTS

BACKGROUND OF THE INVENTION a) Field of the Invention

This invention relates to compounds which have antifungal activities and are useful as drugs or antimicrobial materials, and also to compositions containing the same.

b) Description of the Related Art

Dermatophytosis is reckoned as one of the diseases not overcome even in these modern days, as no reliable therapy or drug has been found yet for its treatment. A large number of compounds have therefore been screened for antifungal activities. All the same, even among substances which have been found to have activities at the in vitro or animal level, all but a few remain after elimination in the actual clinical stage. At present, an extremely small number of substances are known to bring about satisfactory results. Under these circumstances, there has been a long-standing desire for the discovery of a novel base structure having antifungal activities. Incidentally, compounds represented by general formula (1), which will be described subsequently herein, are all novel compounds, to say nothing of their possession of antifungal activities.

With the foregoing circumstances in view, the present invention has as a primary object the finding of a novel base structure having antifungal activities and hence the provision of a novel compound having such antifungal activities.

SUMMARY OF THE INVENTION

Under these circumstances, the present inventors have therefore proceeded with synthesis of a wide variety of compounds and their screening for antifungal activities with a view to finding a novel base structure. As a result, such antifungal activities were found with the group of compounds represented by the formula (1), leading to the completion of the present invention.

Namely, the present invention provides a compound represented by the following formula (1):

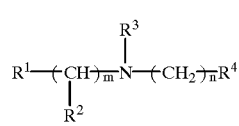

wherein $R^1$ represents a substituted or unsubstituted aromatic hydrocarbon group having 6 to 18 carbon atoms, $R^2$ represents a hydrogen atom or a substituted or unsubstituted aromatic hydrocarbon group having 6 to 18 carbon atoms, $R^3$ represents an alkyl group having 1 to 4 carbon atoms, $R^4$ represents a substituted or unsubstituted phenyl group or an aliphatic hydrocarbon group containing at least four r electrons, and m and n individually represent integers of from 1 to 4; or a salt thereof.

The present invention also provides a composition comprising the compound of the formula (1) or the salt thereof and a carrier.

Further, the present invention also provides a method for the treatment of a mycosis, which comprises administering an effective amount of the compound of the formula (1) or the salt thereof to a patient.

Moreover, the present invention also provides use of the compound of the formula (1) or the salt thereof as a drug.

DETAILED DESCRIPTION OF THE INVENTION AND PREFERRED EMBODIMENTS

Illustrative of the substituted or unsubstituted aromatic hydrocarbon groups having 6 to 18 carbon atoms and represented by $R^1$ and $R^2$ in the formula (1) are unsubstituted aromatic groups having 6 to 18 carbon atoms and phenyl, naphthyl, biphenyl and like groups substituted by one or more halogen atoms, $C_1$–$C_6$ alkyl groups and/or $C_1$–$C_6$ alkoxyl groups. Among these, phenyl or biphenyl is particularly preferred as $R^1$. Further, phenyl is especially preferred as $R^2$.

Examples of the alkyl group represented by $R^3$ can include methyl, ethyl and isopropyl, with methyl being particularly preferred.

Illustrative of the substituted or unsubstituted phenyl group represented by $R^4$ are unsubstituted phenyl groups and phenyl groups substituted by one or more halogen atoms, $C_1$–$C_6$ alkyl groups, $C_1$–$C_6$ alkoxyl groups and/or $C_1$–$C_6$ haloalkyl groups. Specific examples of $R^4$ can include tert-butylphenyl, phenyl, methylphenyl, chlorophenyl and the like, with tert-butylphenyl being particularly preferred.

Illustrative of the aliphatic hydrocarbon group containing at least four π electrons, said group being represented by $R^4$, are $C_5$–$C_{12}$ aliphatic hydrocarbon groups with at least two unsaturated bonds contained therein. $C_5$–$C_{12}$ Aliphatic hydrocarbon groups containing two double bonds per group and $C_5$–$C_{12}$ aliphatic hydrocarbon groups containing one double bond and one triple bond per group are more preferred. Specific examples of these groups can include 5,5-dimethyl-1-hexen-3-yn-1-yl.

m and n individually stand for integers of from 1 to 4, with m=1 and n=1 being especially preferred.

Among the compounds of the formula (1), particularly preferred examples can include 4-tert-butyl-N-methyl-N-(2-phenylbenzyl)benzylamine, 4-tert-butyl-N-methyl-N-(3-phenylbenzyl)benzylamine, 4-tert-butyl-N-methyl-N-(4-phenylbenzyl)benzylamine, 4-tert-butyl-N-diphenylmethyl-N-methylbenzylamine, N-(6,6-dimethyl-2-hepten-4-yn-1-yl)-N-methyl-2-phenylbenzylamine, N-(6,6-dimethyl-2-hepten-4-yn-1-yl)-N-methyl-3-phenylbenzylamine, N-(6,6-dimethyl-2-hepten-4-yn-1-yl)-N-methyl-4-phenylbenzylamine, and N-(6,6-dimethyl-2-hepten-4-yn-1-yl)-N-methyl(diphenylmethyl)amine.

No particular limitation is imposed on the salt of the compound of the formula (1) insofar as it is physiologically acceptable. Preferred examples of such salts can include mineral acid salts such as the hydrochloride, sulfate and nitrate and organic acid salts such as the citrate, maleate, oxalate and tartrate. Among these salts, the hydrochloride is most preferred.

Incidentally, the compound of the formula (1) has isomers with respect to an unsaturated bond and should be considered to include the cis-isomer, the transisomer and mixtures thereof. Further, the compound of the formula (1) in the form of a hydrate, if exists, should also be considered to fall within the present invention.

The compound of the formula (1) can be prepared, for example, by a process represented by the following reaction formula.

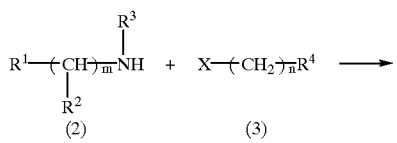

-continued

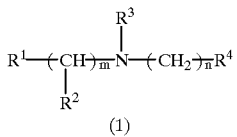

wherein X represents an eliminative group such as a halogen atom or p-toluenesulfonyl group, and $R^1$, $R^2$, $R^3$, $R^4$, m and n have the same meanings as defined above.

Namely, the compound (1) can be obtained by reacting the compound (2) with the compound (3).

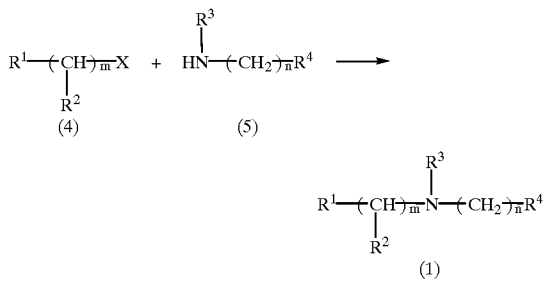

wherein X, $R^1$, $R^2$, $R^3$, $R^4$, m and n have the same meanings as defined above.

Namely, the compound (1) can be obtained by reacting the compound (4) with the compound (5).

The reaction between the compound (2) and the compound (3) and the reaction between the compound (4) and the compound (5) can be conducted preferably in the presence of a base such as sodium carbonate.

On the other hand, the physiologically-acceptable salt of the compound of the formula (1) can be prepared by a method known per se in the art, for example, by mixing the corresponding acid and the compound of the formula (1) in a nonpolar solvent or a polar solvent. The compound, which has been synthesized following the reaction formula, can be easily purified in a usual manner, for example, by using a conventional purification method such as column chromatography making use of silica gel, alumina, an ion-exchange resin or the like as a carrier, liquid-liquid extraction making use of ether-water, chloroform-water, water-containing alcohol-petroleum ether or butanol-water, or recrystallization.

The compounds available as described above are all novel compounds which have not been reported in any publication, and have antifungal activities as will be demonstrated in Examples to be described subsequently herein. Further, the compounds of the present invention are also expected to have high safety. The compounds according to the present invention are therefore useful as antifungal agents in drugs and antifungal materials.

The composition of the present invention comprises the compound (1) and a carrier. Only one of the above-described compounds may be incorporated, or two or more of them may be incorporated in combination. Illustrative of such a composition are pharmaceutical compositions such as external dermal preparations and washing and/or disinfecting external preparations, clothing such as socks, stockings and undershirts, and plastic products such as toothbrushes and ballpoint pens. Among these, pharmaceutical compositions, especially external dermal preparations, are most preferred. To incorporate the compound of the present invention in the composition, a conventional technique can be followed. In the case of a pharmaceutical composition, for example, the compound of the present invention can be emulsified or solubilized together with other ingredients, or it can be mixed in powdery ingredients, followed by granulation. In the case of clothing, it can be mixed in a molten resin prior to spinning upon production of fibers, or the clothing can be impregnated with it. In the case of a plastic product, it is preferable to mix the compound in a molten resin. It is also possible to impregnate wood with the compound so that the wood can be protected from mold.

Examples of the carrier employed in the composition of the present invention can include any desired carriers generally contained in drugs, fibers, plastic materials and the like. Concerning pharmaceutical compositions, illustrative of such desired carriers are excipients, coloring matters, taste or smell corrigents, binders, disintegrators, coating materials, stabilizers, pH regulators, sugar-coating materials, emulsifiers, dispersants, and solubilizers. Especially for external dermal preparations, illustrative examples can include hydrocarbons such as liquid paraffin and vaseline, esters such as spermaceti and bees wax, triglycerides such as olive oil and beef tallow, higher alcohols such as cetanol and oleyl alcohol, fatty acids such as stearic acid and oleic acid, polyhydric alcohols such as propylene glycol and glycerin, nonionic surfactants, anionic surfactants, cationic surfactants, and thickeners. For clothing and plastics, illustrative examples can include plasticizers, crosslinking agents, coloring matters, antioxidants, and ultraviolet absorbers. The content of the compound of the present invention in the composition according to the present invention may range preferably from 0.001 to 20 wt. %, more preferably from 0.01 to 15 wt. %, most preferably from 0.1 to 10 wt. %.

EXAMPLES

The present invention will hereinafter be described in detail by Examples. Needless to say, the present invention shall not be limited to the Examples only.

Synthesis Example 1

Orthophenylbenzoic acid (10 g) and thionyl chloride (18.7 g) were mixed with 100 ml of chloroform, followed by heating for 4 hours under reflux. The reaction mixture was concentrated under reduced pressure, and the resulting concentrate was added dropwise to 40 ml of a 40% aqueous solution of methylamine under ice cooling. The temperature of the resulting mixture was allowed to rise to room temperature, at which a reaction was allowed to proceed under stirring for 4 days. 2 N hydrochloric acid was added to terminate the reaction, followed by the extraction of the resulting mixture with chloroform. The organic layer was washed with a saturated aqueous solution of sodium hydrogencarbonate. The organic layer was collected, from which the solvent was distilled off so that N-methyl-2-phenylbenzoic acid amide was obtained. The acid amide was reduced with 0.54 g of lithium aluminum hydride in diethyl ether, whereby 1.46 g of N-methyl-2-phenylbenzylamine were obtained. The benzylamine was reacted with an acid chloride, which had been derived from 1.45 g of p-tert-butylbenzoic acid, in the presence of triethylamine in benzene. Water and chloroform were added to the reaction mixture for extraction. The organic layer was collected and was then washed successively with dilute hydrochloric acid, a saturated aqueous solution of sodium hydrogencarbonate, water and a saturated aqueous solution of sodium chloride in the order that they are presented. The solvent was distilled off, whereby 2.42 g of N-methyl-N-(2-phenylbenzyl)-4-tert-butylbenzoic acid amide were obtained as yellow crystals. The acid amide was reduced with lithium aluminum hydride in tetrahydrofuran and the reduction product was extracted with diethyl ether, whereby 0.83 g of 4-tert-butyl-N-methyl-N-(2-phenylbenzyl)benzylamine (Compound 1) was obtained (yield: 35.7%). The following is its NMR spectrum data.

$^1$H-NMR (CDCl$_3$,δ ppm): 1.31(9H,s), 2.10(2H,s), 3.44 (2H,s), 7.17–7.69(13H,m).

Compound 1 was dissolved in 20 ml of diethyl ether, to which a 4 N solution of hydrochloric acid in ethyl acetate was added dropwise. Diethyl ether (160 ml) was added, and the resulting white precipitate was collected by filtration. The white precipitate was recrystallized from a mixed solvent of diethyl ether and ethanol, whereby 0.48 g of white crystals was obtained (yield: 52.5%). Melting point: 147–149° C. The following is its NMR spectrum data.

$^1$H-NMR (CDCl$_3$,δ ppm): 1.29(9H,s), 2.3(3H,d), 3.80–4.06(2H,m), 4.18–4.33(2H,m), 7.16–8.28(13H,m), 12.4(1H,s).

Further, the following is its IR spectrum data:
IR (KBr,cm$^{-1}$): 3419, 2961, 2905, 1476, 755, 704.

Synthesis Example 2 p-tert-butylbenzoic acid (10.1 g) and thionyl chloride (20.2 g) were mixed with 100 ml of chloroform, followed by heating under reflux for 5 hours. After the solvent and the remaining thionyl chloride were distilled off under reduced pressure, the residue was dissolved in 10 ml of chloroform. The resulting chloroform solution was added dropwise to 17 ml of a 40% solution of methylamine in methanol under ice cooling. The temperature of the resulting mixture was allowed to rise to room temperature, at which the mixture was stirred for 48 hours. To the reaction mixture, 100 ml of 2 N hydrochloric acid were added. The resulting mixture was extracted with 100 ml of dichloromethane, and the organic layer was added first with water and then with a saturated aqueous solution of sodium chloride so that the organic layer was washed. The organic layer was washed further with a saturated aqueous solution of sodium hydrogencarbonate and the solvent was distilled off, whereby N-methyl-4-tert-butylbenzoic acid amide was obtained. The acid amide was dissolved in 100 ml of diethyl ether. After 3 g of lithium aluminum hydride were mixed, the resulting mixture was heated for 6 hours under reflux under a nitrogen gas atmosphere. After water was added under ice cooling to terminate the reaction, the insoluble matter was collected by filtration and was then washed with diethyl ether. The filtrate and the washing were combined and then washed with water, and the solvent was dissolved off under reduced pressure, whereby 3.69 g of N-(4-tert-butylbenzyl)methylamine were obtained. On the side, 9.83 g of 3-phenyltoluene were dissolved in 100 ml of carbon tetrachloride, followed by the addition of 10.5 g of N-bromosuccinimide and 150 mg of benzoyl peroxide. The resulting mixture was heated for 3 hours under reflux. The reaction mixture was allowed to cool down. The insoluble matter was filtered off. Subsequent to concentration of the filtrate, the resulting concentrate was purified by chromatography on a silica gel column (eluent: hexane/ethyl acetate=10/1), whereby 6.51 g of 3-(bromomethyl)biphenyl were obtained (yield: 45%). N-(4-tert-butylbenzyl)methylamine (2.78 g) and the 3-(bromomethyl)biphenyl were reacted at room temperature for 24 hours in the presence of sodium carbonate in N,N-dimethylformamide. The reaction mixture was extracted with chloroform and a saturated aqueous solution of sodium chloride. The organic layer was collected and then concentrated. The resulting concentrate was purified by chromatography on a silica gel column (eluent:hexane/chloroform=9/1), whereby 2.97 g of 4-tert-butyl-N-methyl-N-(3-phenylbenzyl)benzylamine (Compound 2) were obtained as a yellow oil (yield: 60.9%). Melting point: 175–176° C. The following is its NMR spectrum data.

$^1$H-NMR (CDCl$_3$,δ ppm): 1.26 (9H,s), 2.18(3H,s), 3.49 (2H,s), 3.54(2H,s), 7.23–7.59(13H,m).

Its hydrochloride was also prepared in a similar manner as in Synthesis Example 1. Yield: 2.71 g (82.5%). The followings are its NMR spectrum data and IR spectrum data:

$^1$H-NMR (CDCl$_3$,δ ppm): 1.33(9H,s), 2.61(3H,d), 4.04–4.14(2H,m), 4.24–4.37(2H,m), 7.35–7.84(13H,m), 12.9(1H,s).

IR (KBr,cm$^{-1}$): 2960, 2515, 1460, 459, 701.

Synthesis Example 3

In a similar manner as in Synthesis Example 1, 0.63 g of 4-tert-butyl-N-methyl-N-(4-phenylbenzyl)benzylamine (Compound 3) was obtained as a yellow oil from 2.47 g of p-phenylbenzoic acid. The following is its NMR spectrum data:

$^1$H-NMR (CDCl$_3$,δ ppm): 1.32(9H,s), 2.16(3H,s), 3.48 (2H,s), 3.50(2H,s), 7.29–7.65(13H,s).

Its hydrochloride was also prepared in a similar manner as in Synthesis Example 1. Yield: 0.51 g (73.1%). Melting point: ≧230° C. The followings are its NMR spectrum data and IR spectrum data:

$^1$H-NMR (CDCl$_3$,δ ppm): 1.33(9H,s), 2.59(3H,s), 4.10 (2H,s), 4.27(2H,d), 7.36–7.73(13H,m), 12.6(1H,s).

IR (KBr,cm$^{-1}$): 3428, 2960, 2614, 2566, 1466, 763.

Synthesis Example 4

In a similar manner as in Synthesis Example 2, 0.83 g of 4-tert-butyl-N-diphenylmethyl-N-methylbenzylamine (Compound 4) was obtained as an oil from 4.06 g of chlorodiphenylmethane. The following is its NMR spectrum data:

$^1$H-NMR (CDCl$_3$,δ ppm): 1.29(9H,s), 2.06(3H,s), 3.46 (2H,s), 4.45(1H,s), 7.09–7.50(14H,m).

Its hydrochloride was also prepared in a similar manner as in Synthesis Example 1. Yield: 0.47 g (51.1%). Melting point: ≧220° C. The followings are its NMR spectrum data and IR spectrum data:

$^1$H-NMR (CDCl$_3$,δ ppm): 1.35(9H,s), 2.57(3H,d), 4.38 (2H,s), 4.83(1H,d), 7.21–8.05(14H,m), 13.2(1H,s).

IR (KBr,cm$^{-1}$): 3412, 2969, 2473, 1457, 908, 707.

Synthesis Example 5

N-methyl-2-phenylbenzylamine (2.57 g) was dissolved in 17 ml of N,N-dimethylformamide (DMF), followed by the addition of 1.39 g of sodium carbonate. While stirring the resulting mixture under ice cooling, a solution of 2.5 g of 1-bromo-6,6-dimethyl-2-hepten-4-yne in DMF was added dropwise. The temperature of the mixture was allowed to rise to room temperature, at which a reaction was allowed to proceed for 16 hours. After the reaction mixture was concentrated under reduced pressure, water and diethyl ether were added to subject the resulting concentrate to liquid-liquid extraction. The organic layer was collected and then dried over magnesium sulfate. The solvent was then distilled off. The residue was purified by chromatography on a silica gel (eluent:hexane/ethyl acetate=10/1), whereby trans-N-(6,6-dimethyl-2-hepten-4-yn-1-yl)-N-methyl-2-phenylbenzylamine (Compound 5) and cis-N-(6,6-dimethyl-2-hepten-4-yn-1-yl)-N-methyl-2-phenylbenzylamine (Compound 6) were obtained in amounts of 2.15 g (yield: 54.5%) and 0.73 g (yield: 18.5%), respectively. The followings are their NMR spectrum data:

$^1$H-NMR (CDCl$_3$,δ ppm) of Compound 5: 1.25(9H,s), 2.08(3H,s), 2.92(2H,dd), 3.40(2H,s), 5.55(1H,dt), 5.93(1H, dt), 7.20–7.45(8H,m), 7.56(1H,dd).

$^1$H-NMR (CDCl$_3$,δ ppm) of Compound 6: 1.21(9H,s), 2.12(3H,s), 3.16(2H,dd), 3.49(2H,s), 5.53(1H,dt), 5.78(1H, dt), 7.2–7.48(8H,m), 7.58(1H,dd).

Compound 5 (2.15 g) was dissolved in 7 ml of ethyl acetate, followed by the dropwise addition of a 4 N solution of hydrochloric acid in ethyl acetate. Diethyl ether (160 ml) was added and the resulting white precipitate was collected by filtration, whereby 2.15 g of the hydrochloride of Compound 5 were obtained as white crystals (yield: 89.7%). Melting point: 174–175.5° C. The following is its NMR spectrum data:

$^1$H-NMR (CDCl$_3$,δ ppm): 1.25(9H,s), 2.39(3H,d), 3.28 (1H,m), 3.45–3.6(1H,m), 4.16(1H,dd), 4.30(1H,dd), 5.64 (1H,d), 5.95(1H,dt), 7.25(2H,m), 7.33(1H,dd), 7.4–7.63(5H, m), 8.22(1H,dd), 12.55(1H,s).

Compound 6 (730 mg) was processed in a similar manner as in Synthesis Example 1, whereby 610 mg of the hydrochloride of Compound 6 were obtained (yield: 74.9%). Melting point: 112–116° C. The following is its NMR spectrum data:

$^1$H-NMR (CDCl$_3$,δ ppm): 1.16(9H,s), 2.38(3H,dd), 3.45–3.73(2H,m), 4.19(1H,dd), 4.35(1H,dd), 5.83(1H,d), 6.06(1H,dt), 7.24(2H,m), 7.34(1H,dd), 7.4–7.6(5H,m), 8.21 (1H,dd), 12.47(1H,br).

Synthesis Example 6

3-Phenylbenzylamine (3.93 g) was processed in a similar manner as in Synthesis Example 5, whereby trans-N-(6,6-dimethyl-2-hepten-4-yn-1-yl)-N-methyl-3-phenylbenzylamine (Compound 7) and cis-N-(6,6-dimethyl-2-hepten-4-yn-1-yl)-N-methyl-3-phenylbenzylamine (Compound 8) were obtained in amounts of 2.73 g (yield: 45%) and 0.72 g (yield: 11.9%), respectively. The followings are their NMR spectrum data:

$^1$H-NMR (CDCl$_3$,δ ppm) of Compound 7: 1.24(9H,s), 2.22(3H,s), 3.08(2H,dd), 3.55(3H,s), 5.66(1H,dt), 6.11(1H, dt), 7.25–7.68(9H,m).

$^1$H-NMR (CDCl$_3$,δ ppm) of Compound 8: 1.24(9H,s), 2.26(3H,s), 3.31(2H,dd), 3.59(3H,s), 5.63(1H,dt), 5.97(1H, dt), 7.26–7.67(9H,m).

Compounds 7 and 8 (2.70 g and 0.72 g) were processed in a similar manner as in Synthesis Example 1, whereby their hydrochlorides were obtained in amounts of 2.77 g (yield: 92%) and 0.6 g (yield: 74.7%). The melting point of the hydrochloride of Compound 7 was 183–185° C., while that of the hydrochloride of compound 8 was 133.5–135° C. The followings are their NMR spectrum data:

$^1$H-NMR (CDCl$_3$,δ ppm) of the hydrochloride of Compound 7: 1.25(9H,s), 2.67(3H,d), 3.58(1H,m), 3.78(1H,m), 4.09(1H,dd), 4.3(1H,dd), 5.86(1H,d), 6.30(1H,dt), 7.3–7.8 (8H,m), 7.85(1H,bs), 13.01(1H,br).

$^1$H-NMR (CDCl$_3$,δ ppm) of the hydrochloride of Compound 8: 1.19(9H,s), 2.68(3H,d), 3.85(2H,m), 4.15(1H,m), 4.37(1H,m), 5.99(1H,d), 6.31(1H,m), 7.35–7.78(8H,m), 7.81(1H,bs), 12.99(1H,br).

Synthesis Example 7

N-methyl-4-phenylbenzylamine (0.75 g) was processed in a similar manner as in Synthesis Example 5, whereby trans-N-(6,6-dimethyl-2-hepten-4-yn-1-yl)-N-methyl-4-phenylbenzylamine (Compound 9) and cis-N-(6,6-dimethyl-2-hepten-4-yn-1-yl)-N-methyl-4-phenylbenzylamine (Compound 10) were obtained in amounts of 0.52 g (yield: 45%) and 0.12 g (yield: 10.4%), respectively. The followings are their NMR spectrum data:

$^1$H-NMR (CDCl$_3$,δ ppm) of Compound 9: 1.24(9H,s), 2.22(3H,s), 3.08(2H,dd), 3.53(3H,s), 5.67(1H,d), 6.11(1H, dt), 7.25–7.67(9H,m).

$^1$H-NMR (CDCl$_3$,δ ppm) of Compound 10: 1.25(9H,s), 2.26(3H,s), 3.31(2H,dd), 3.58(2H,s), 5.64(1H,dt), 5.98(1H, dt), 7.3–7.64(9H,m).

From 0.52 g of Compound 9, 0.52 g of its hydrochloride was prepared in a similar manner as in Synthesis Example 1 (yield: 89.7%). Melting point: 196.5–198° C. The following is its NMR spectrum data:

$^1$H-NMR (CDCl$_3$,δ ppm): 1.25(9H,s), 2.67(3H,d), 3.55 (1H,m), 3.75(1H,m), 4.09(1H,m), 4.24(1H,m), 5.87(1H,dt), 6.30(1H,dt), 7.35–7.55(3H,m), 7.57–7.64(2H,m), 7.72(4H, bs), 12.96(1H,br).

Synthesis Example 8

N-(diphenylmethyl)methylamine (2.0 g) was processed in a similar manner as in Synthesis Example 5, whereby 2.90 g of N-(6,6-dimethyl-2-hepten-4-yn-1-yl)-N-methyl (diphenylmethyl)amine (Compound 11) were obtained. It was processed in a similar manner as in Synthesis Example 1, whereby 2.10 g of its hydrochloride were obtained as white crystals (yield: 61.5%). Melting point: 222–224° C. The following is its NMR spectrum data:

$^1$H-NMR (CDCl$_3$,δ ppm): 1.26(9H,s), 2.68(3H,d), 3.64 (1H,m), 3.86(1H,m), 4.85(1H,d), 5.71(1H,d), 6.10(1H,dt), 7.28–7.5(6H,m), 7.87(4H,m), 13.21(1H,br).

Example 1

In accordance with the formulation shown below, compositions which contained polystyrene and the corresponding compounds of the present invention, respectively, were prepared. Described specifically, toothbrush handles of each composition were produced by mixing polystyrene beads and the corresponding compound of the present invention and then subjecting the resulting mixture to melt forming.

| Polystyrene beads | 99 parts by weight |
|---|---|
| One of Compounds 1–11 | 1 part by weight |

Example 2

In accordance with the formulation shown below, compositions which contained polystyrene and the corresponding compounds of the present invention, respectively, were prepared. Described specifically, toothbrush handles of each composition were produced by mixing polystyrene beads and the hydrochloride of the corresponding compound of the present invention and then subjecting the resulting mixture to melt forming.

| Polystyrene beads | 90 parts by weight |
|---|---|
| One of hydrochlorides of Compounds 1–11 | 10 parts by weight |

Example 3

In accordance with the formulation shown below, compositions which contained polystyrene and the corresponding compounds of the present invention, respectively, were prepared. Described specifically, ballpoint pen barrels of each composition were produced by mixing polystyrene beads and the corresponding compound of the present invention and then subjecting the resulting mixture to melt forming.

| Polystyrene beads | 99.9 parts by weight |
|---|---|
| One of Compounds 1–11 | 0.1 part by weight |

Example 4

In accordance with the formulation shown below, compositions which contained polystyrene and the corresponding compounds of the present invention, respectively, were prepared. Described specifically, ballpoint pen barrels of each composition were produced by mixing polystyrene beads and the hydrochloride of the corresponding compound of the present invention and then subjecting the resulting mixture to melt forming.

| Polystyrene beads | 99 parts by weight |
|---|---|
| One of hydrochlorides of Compounds 1–11 | 1 part by weight |

Example 5

In accordance with the formulation shown below, ointments were obtained for the treatment of athlete's foot. Described specifically, an ointment of each composition was obtained by weighing the corresponding ingredients, charging them into a kneader and then kneading them there.

| Vaseline | 99 parts by weight |
|---|---|
| One of hydrochlorides of Compounds 1–11 | 1 part by weight |

Example 6

In accordance with the formulation shown below, ointments were obtained for the treatment of athlete's foot. Described specifically, an ointment of each composition was obtained by weighing the corresponding ingredients, charging them into a kneader and then kneading them there.

| Absorption ointment | 99 parts by weight |
|---|---|
| One of Compounds 1–11 | 1 part by weight |

Example 7

Liquid preparations were obtained by stirring and solubilizing the corresponding ingredients shown below.

| Ethanol | 92 parts by weight |
|---|---|
| Alkyl methacrylate copolymer | 2 parts by weight |
| One of Compounds 1–11 | 1 part by weight |
| Propylene glycol | 5 parts by weight |

Test 1

Antifungal Activity Test (Measurement of Minimum Inhibitory Concentration)

Antifungal activities of compounds according to the present invention against Trichophyton sp. were determined. Described specifically, *T. mentagrophytes* (TIMM1189) was cultured at 27° C. for 2 weeks on Sabouraud dextrose agar slants in advance, whereby it was allowed to form sufficient conidia. The conidia were washed in a sterilized physiological saline, which contained Tween 80 at a concentration of 0.05 wt./vol. %, by rubbing the conidia with a platinum loop, whereby the conidia were suspended. The suspension was filtered through a double-layer gauze so that only the conidia were collected in a form suspended in the physiological saline. The suspension was diluted to adjust the concentration of conidia to $1 \times 10^5$ conidia/ml, whereby a test fungus solution was obtained. Meanwhile, 4 mg of one of the test compounds were taken, to which 1 ml of dimethyl sulfoxide was added to prepare a stock. The stock was subjected to doubling dilution with ethanol to prepare diluted drug solutions. To each well of a 96-well microplate for tissue culture, 175 μl of Sabouraud dextrose broth, 5 μl of the corresponding drug solution and 20 μl of the test fungus solution were added. Subsequent to thorough mixing, the fungus strain was cultured at 27° C. for 1 week. A minimum concentration at which its growth was completely inhibited was visually determined and was recorded as a minimum inhibitory concentration (MIC). As a result, the compounds according to the present invention have been found to have excellent antifungal activities as shown in Table 1.

TABLE 1

| Sample | MIC (μg/ml) |
|---|---|
| Compound 1 | 12.5 |
| Compound 2 | 25 |
| Compound 3 | 12.5 |
| Compound 4 | 100 |
| Compound 5 | 12.5 |
| Compound 6 | 100 |
| Compound 7 | 12.5 |
| Compound 8 | 12.5 |
| Compound 9 | 12.5 |
| Compound 11 | 100 |

What is claimed is:

1. A compound represented by the following formula (1):

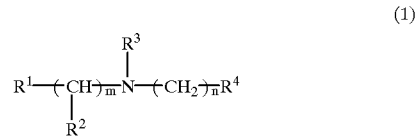

wherein $R^1$ represents an unsubstituted phenyl group, an unsubstituted biphenyl group, or a phenyl or biphenyl group substituted by one or more halogen atoms, $C_{1-6}$ alkyl groups and/or $C_{1-6}$ alkoxy groups, $R^2$ represents a hydrogen atom or an unsubstituted phenyl group, an unsubstituted biphenyl group, or a phenyl or biphenyl group substituted by one or more halogen atoms, $C_{1-6}$ alkyl groups and/or $C_{1-6}$ alkoxy groups, $R^3$ represents an alkyl group having 1 to 4 carbon atoms, $R^4$ represents a substituted or unsubstituted phenyl group or an aliphatic hydrocarbon group containing at least four π electrons, and m and n individually represent integers of from 1 to 4; or a salt thereof.

2. A compound or a salt thereof according to claim 1, wherein $R^4$ represents a phenyl group which may be substituted by one or more alkyl groups having 1 to 6 carbon atoms, or a $C_5$–$C_{12}$ aliphatic hydrocarbon group containing two unsaturated bonds; and m and n individually represent 1.

3. A compound or a salt thereof according to claim 1, which is 4-tert-butyl-N-methyl-N-(2-phenyl-benzyl)benzylamine, 4-tert-butyl-N-methyl-N-(3-phenylbenzyl)benzylamine, 4-tert-butyl-N-methyl-N-(4-phenylbenzyl)benzylamine, 4-tert-butyl-N-diphenylmethyl-N-methylbenzylamine, N-(6,6-dimethyl-2-hepten-4-yn-1-yl)-N-methyl-2-phenylbenzylamine, N-(6,6-dimethyl-2-hepten-4-yn-1-yl)-N-methyl-3-phenylbenzylamine, N-(6,6-dimethyl-2-hepten-4-yn-1-yl)-N-methyl-4-phenylbenzylamine, or N-(6,6-dimethyl-2-hepten-4-yn-1-yl)-N-methyl-(diphenylmethyl)amine; or a salt thereof.

4. A composition comprising a compound or a salt thereof according to any one of claims 1–3 and a carrier.

5. A composition according to claim 4, which is a pharmaceutical composition.

6. A method for the treatment of a mycosis, which comprises administering an effective amount of a compound or a salt thereof according to any one of claims 1–3 to a patient.

* * * * *